US006531318B1

(12) United States Patent
Palmer-Toy et al.

(10) Patent No.: US 6,531,318 B1
(45) Date of Patent: Mar. 11, 2003

(54) METHODS AND APPARATUS FOR CELL ANALYSIS

(75) Inventors: Darryl E. Palmer-Toy, Arlington, MA (US); David Sarracino, Medford, MA (US); Dennis Sgroi, Winchester, MA (US); Peter Leopold, Cambridge, MA (US)

(73) Assignees: The General Hospital Corporation, Boston, MA (US); ProteiGene, Inc., Billerica, MA (US)

( * ) Notice: Subject to any disclaimer, the term of this patent is extended or adjusted under 35 U.S.C. 154(b) by 126 days.

(21) Appl. No.: 09/684,060

(22) Filed: Oct. 6, 2000

Related U.S. Application Data

(60) Provisional application No. 60/158,567, filed on Oct. 8, 1999.

(51) Int. Cl.[7] .......................... G01N 33/48; G01N 24/00
(52) U.S. Cl. .......................... 436/63; 436/64; 436/173; 435/40.5; 435/40.51; 435/40.52; 435/29; 250/281; 250/282; 250/288
(58) Field of Search .......................... 436/63, 173, 64; 435/40.5, 40.51, 40.52, 4, 29, 1.1, 6; 250/281, 282, 288

(56) References Cited

U.S. PATENT DOCUMENTS

| 5,808,300 | A | | 9/1998 | Caprioli ...................... 250/288 |
| 5,843,657 | A | | 12/1998 | Liotta et al. .................... 435/6 |
| 5,985,085 | A | | 11/1999 | Baer et al. .................... 156/285 |
| 6,071,610 | A | * | 6/2000 | Jarrell et al. ................. 428/335 |
| 6,184,973 | B1 | * | 2/2001 | Baer et al. ..................... 356/36 |
| 6,215,550 | B1 | * | 4/2001 | Baer et al. ..................... 356/36 |

OTHER PUBLICATIONS

James, "Breakthroughs and Views of Genomes and Proteomes", *Biochemical and Biophysical Research Communications*, 231:1–6, 1997.

Jungblut et al., "Proteomics in human disease: Cancer, heart and infectious diseases", *Electrophoresis*, 20:2100–2110, 1999.

Palmer–Toy et al., "Direct Acquisition of Matrix–assisted Laser Desorption/Ionization Time–of–Flight Mass Spectra from Laser Capture Microdissected Tissues", *Clinical Chemistry*, 46:1513–1516, Sep., 2000.

Simone et al., "Laser–capture microdissection: opening the microscopic frontier to molecular analysis", *Trends in Genetics*, 14:272–276, Jul., 1998.

Suarez–Quian et al., "Laser Capture Microdissection of Single Cells from Complex Tissues", *BioTechniques*, 26:328–335, Feb., 1999.

Bonner et al., "Laser Capture Microdissection: Molecular Analysis of Tissue", *Science*, 278:1481, 1483, Nov. 21, 1997.

Caprioli et al., "Molecular Imaging of Biological Samples: Localization of Peptides and Proteins Using MALDI–TOF MS", *Analytical Chemistry*, 69:4751–4760, Dec. 1, 1997.

Garden et al., "Excess Salt Removal with Matrix Rinsing: Direct Peptide Profiling of Neurons from Marine Invertebrates Using Matrix–assisted Laser Desorption/Ionization Time–of–flight Mass Spectrometry", *Journal of Mass Spectrometry*, 31:1126–1130, 1996.

Klimek et al., "Biochemical microanalysis of pyruvate kinase activity in preneoplastic and neoplastic liver lesions induced in rats by N–nitrosomorpholine", *Carcinogenesis*, 11:1377–1380, Aug., 1990.

(List continued on next page.)

*Primary Examiner*—Maureen M. Wallenhorst
(74) *Attorney, Agent, or Firm*—Fish & Richardson PC

(57) ABSTRACT

A highly specific and sensitive technique for exploring cell physiology is disclosed. The method includes laser capture microdissection (LCM) for selecting small clusters of cells of interest from sections of tissue and matrix-assisted laser desorption ionization mass spectrometry (MALDI-MS) for characterizing simultaneously a broad variety of biological molecules present in the small cluster of cells.

23 Claims, 16 Drawing Sheets

OTHER PUBLICATIONS

Stoeckli et al., "Automated Mass Spectrometry Imaging with a Matrix–Assisted Laser Desorption Ionization Time–of–Flight Instrument", *J. Am. Soc. Mass. Spectrom.*, 10:67–71, 1999.

van Adrichem et al., "Investigation of Protein Patterns in Mammalian Cells and Culture Supernatants by Matrix–Assisted Laser Desorption/Ionization Mass Spectrometry", *Analytical Chemistry*, 70:923–930, Mar. 1, 1998.

* cited by examiner

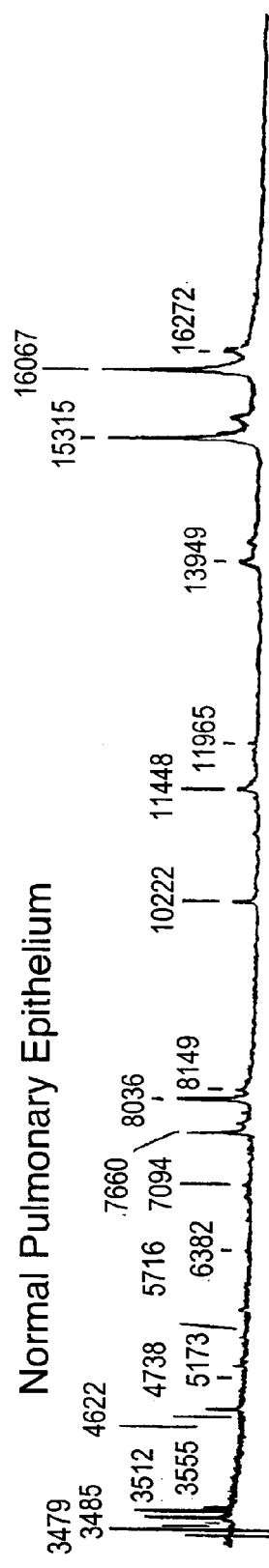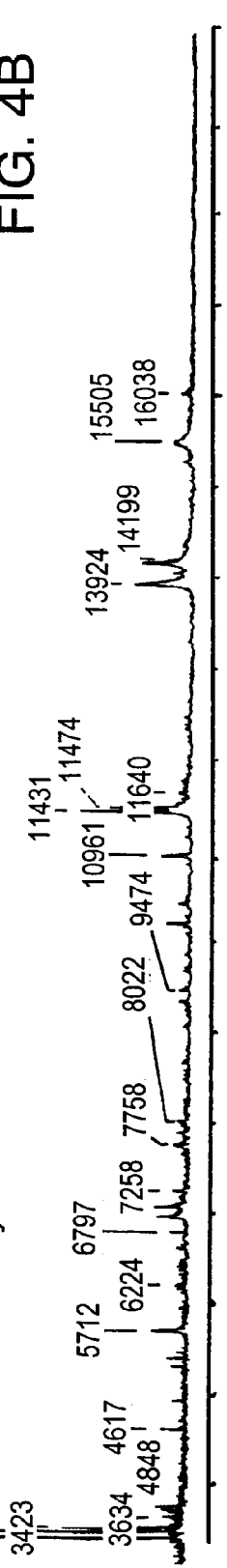
FIG. 4A Normal Pulmonary Epithelium
FIG. 4B Pulmonary Adenocarcinoma
Normal & Malignant Pulmonary Epithelium

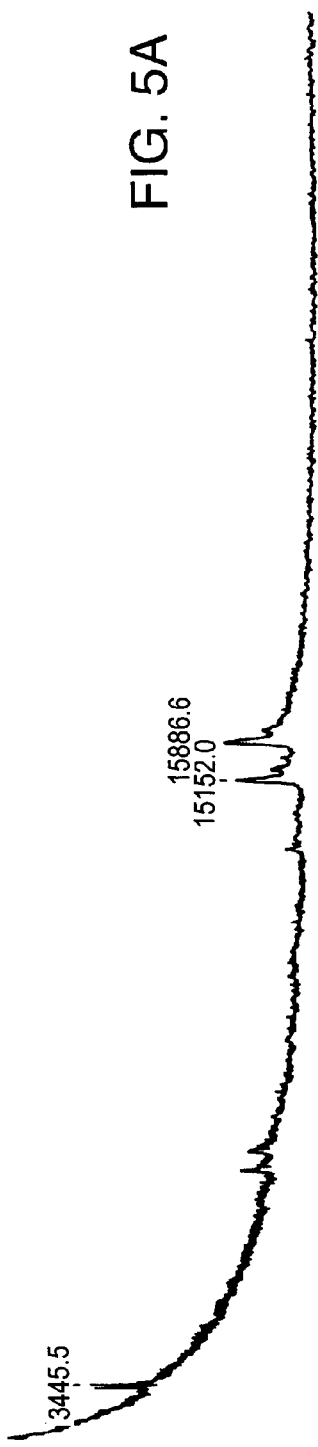
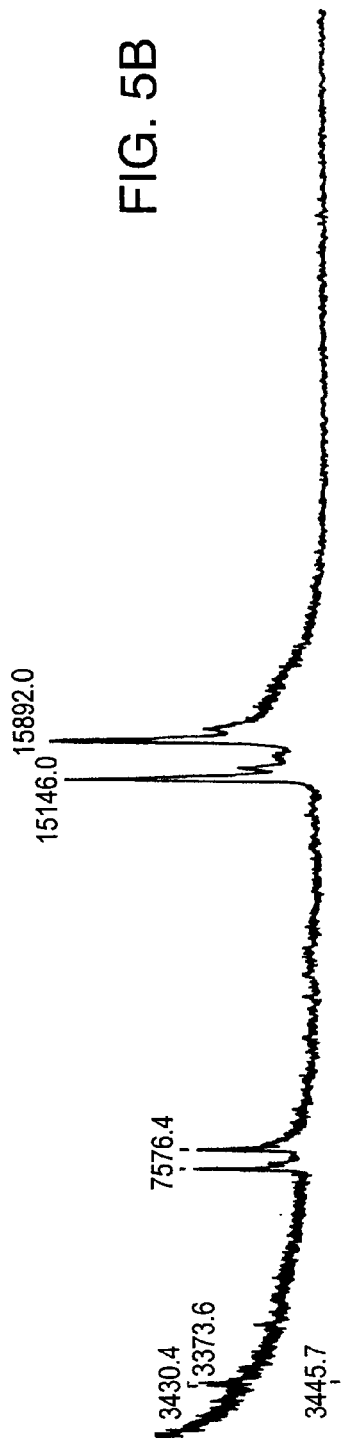
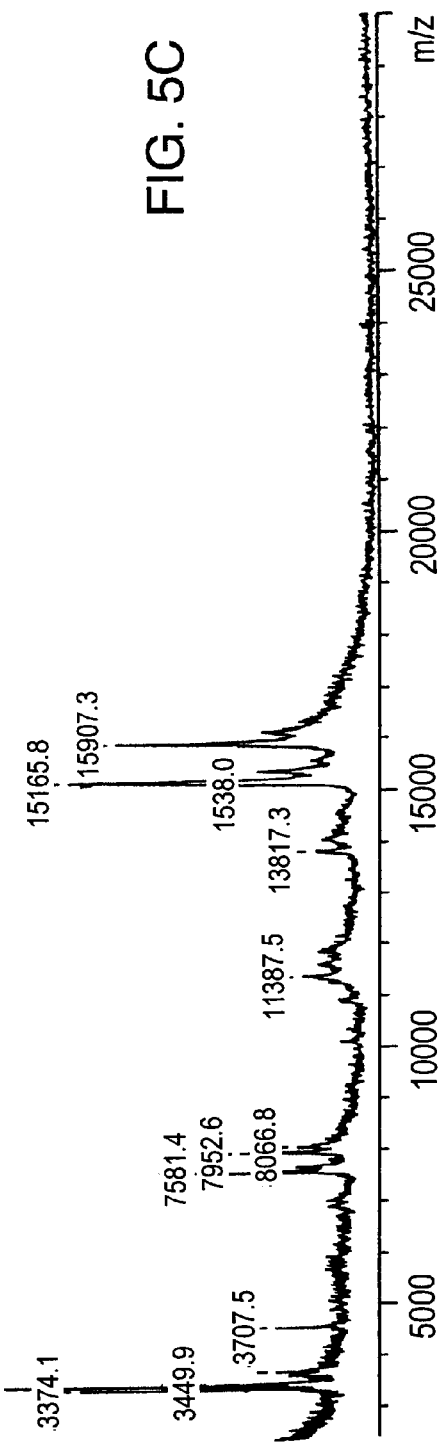
FIG. 5A
FIG. 5B
FIG. 5C

NORMAL BREAST STROMA

FROZEN TISSUE SECTION

LCM CAPTURED

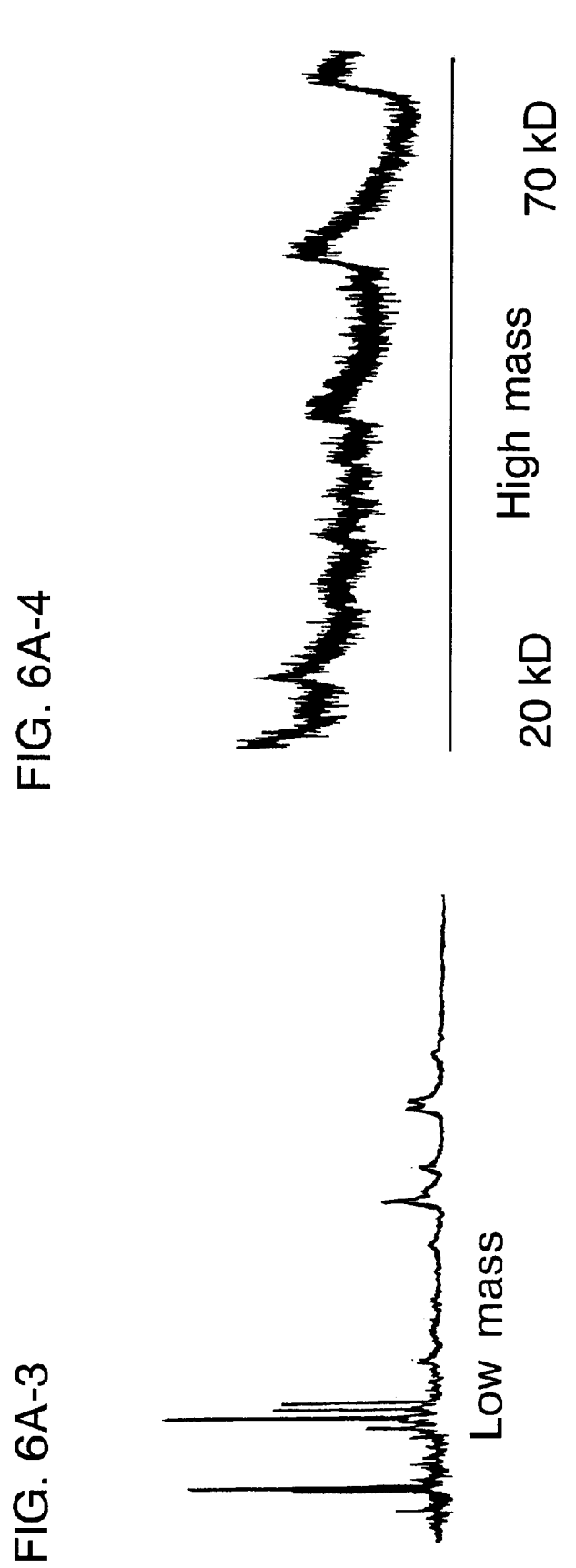

NORMAL BREAST EPITHELIUM

FROZEN TISSUE SECTION

LCM CAPTURED

BREAST CARCINOMA in situ

FROZEN TISSUE SECTION

LCM CAPTURED

INVASIVE BREAST CARCINOMA

FROZEN TISSUE SECTION

LCM CAPTURED

METASTATIC (FROM BREAST) LYMPH NODE CARCINOMA

FROZEN TISSUE SECTION

LCM CAPTURED

METHODS AND APPARATUS FOR CELL ANALYSIS

CROSS-REFERENCE TO RELATED APPLICATION

This application claims benefit of U.S. Provisional Application No. 60/158,567, filed on Oct. 8, 1999, which is incorporated herein by reference in its entirety.

TECHNICAL FIELD

The invention relates to a specific and a sensitive technique for exploring cell physiology.

BACKGROUND

Due to recent advances in genomics more attention is being paid to the protein products of genes as the engines of cell physiology and targets for drug development. The study of protein gene products is termed proteomics. Pathologists often require studies of specific protein expression by various cell types by the techniques of immunohistochemistry and flow cytometry. The recent advent of laser capture micro-dissection has enabled pathologists and researchers in genomics and proteomics to separate clusters of cells or even individual cells of interest from a background of millions of other cells. The collected cells could be directly visualized to verify their identity and purity.

Genetics of the separated cells, typically, is studied using PCR, but to explore the physiology of these cells, and in particular global protein expression, more laborious and less sensitive tools such as Western Blots were necessary.

SUMMARY

The invention is based on the discovery that by selecting specific clusters of cells of interest from sections of a tissue sample by embedding them in a polymer film; removing the polymer film from the tissue sample; and characterizing the specific cells within the polymer film by mass spectroscopy, one obtains the beneficial results of a highly specific and sensitive technique for exploring cell physiology.

The highly specific and sensitive technique for exploring cell physiology includes selecting specific cells by laser capture microdissection (LCM) and characterizing the specific cells by Matrix-Assisted Laser Desorption/Ionization Mass Spectrometry (MALDI-MS).

In one aspect, the invention features a method of determining a mass spectrum, and thereafter a mass spectrometric biochemical profile, of a tissue sample by covering a tissue sample with a polymer (e.g., attached to a substrate), identifying one or more specific cells of the tissue sample for mass spectrometric analysis, melting a portion of the polymer to cause the portion of the polymer to adhere onto the specified cells of the tissue sample and allowing the polymer to solidify, removing the polymer (or at least a portion), the melted portions of which contain the specified cells, attaching the polymer to a mass spectrometric target, applying a matrix composition to the specified cells, and determining the mass spectrum of the specified cells by matrix assisted laser desorption ionization mass spectrometry. For example, the polymer can be removed (e.g., peeled) from the substrate and then attached (e.g., bonded with glue) to the target.

Mass spectrometric biochemical profiles are mass spectra, or derivatives of the mass spectra, of mixtures of biomolecules (taken from a tissue sample) that indicate the identities of some or all of the molecular constituents of the mixture. In applications to some part of or all of living organisms, the mass spectrometric biomolecular profiles reveal, either directly or indirectly, some aspect of the identity or the physiological state of the organism. For example, as described in further detail below, the mass spectrometric biochemical profiles of laser capture microdissected breast tissues indicate the presence or absence of pathological physiology (cancer) of the tissues. The profiles are created from the mass spectra, e.g., by removing background or irrelevant data, normalizing the spectra, or otherwise processing the spectra to produce useful data that can be used to distinguish diseased from normal tissues, e.g., by comparing the profiles with libraries of profiles of normal and diseased tissues.

In another aspect, the invention features a method of determining a mass spectrum of a tissue sample by selecting specific cells of the tissue sample by laser capture microdissection, and determining the mass spectrum of the selected cells by matrix assisted laser desorption ionization mass spectrometry. Determining the mass spectrum of the selected cells can include applying a matrix composition to the selected cells. Determining the mass spectrum also can include ionizing the selected cells on a polymer, e.g., a thermoplastic polymer. Embodiments of these aspects of the invention can include one or more of the following features. The matrix composition can include a proton donor acid. The proton donor acid can be selected from the group consisting of sinapinic acid, 2,5 dihydroxybenzoic acid, alpha-cyano-4-hydroxy cinnamic acid, nicotinic acid, and ferrulic acid. The matrix composition also can include acetonitrile. The mass spectrum further can be determined by ionizing the selected cells on the polymer, or by separating gas-phase ions by time-of-flight (TOF) measurements, ion-trap measurements, magnetic-sector measurements, quadrupole mass filter measurements, or ion cyclotron resonance measurements.

In another aspect, the invention features methods of characterizing tissue samples by selecting specific cells of the tissue sample by laser capture microdissection, determining the mass spectrum, and then a mass spectrometric biochemical profile, of the selected cells by matrix assisted laser desorption ionization mass spectrometry, and comparing the mass spectrum or mass spectrometric biochemical profile of the selected cells against a standard library of mass spectra or spectrometric biochemical profiles of tissue samples. The invention also includes methods of determining whether a tissue sample includes cancer cells, by characterizing the tissue sample as described herein, wherein the library of mass spectra includes spectra of both normal and cancerous tissues.

The tissue samples can be selected from the group consisting of normal breast stroma, normal breast epithelial, breast carcinoma in situ, invasive breast carcinoma, and metastatic lymph node carcinoma. The tissue sample can be a biopsy, e.g., a frozen biopsy, a resected tissue section, and can be normal or diseased.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides one or more of the following advantages. The LCM/MALDI-MS technique is useful to rapidly produce high resolution mass spectra of specific cells from a tissue sample and, in some embodiments, individual cells. Moreover, mass spectra of the tissue samples are recorded by ionizing the sample on a polymer substrate thereby eliminating the need of adhering tissue samples directly to metal target plates.

The technique also allows the study of specific cell types in their native environments, i.e., the specific cells are maintained in their respective cellular location. More importantly, LCM typically separates cells along cell boundaries, and allows visual confirmation that only the desired cells are collected.

Furthermore, the new method allows pooling of material from similar cells to improve capacity of mass spectroscopic detection for low abundance molecular species.

Other features and advantages of the invention will be apparent from the following detailed description, and from the claims.

BRIEF DESCRIPTION OF THE DRAWINGS

FIG. 4A is a mass spectrum of normal human lung epithelial cells.

FIG. 4B is a mass spectrum of malignant human lung epithelial cells from a pulmonary adenocarcinoma.

FIG. 5A is a mass spectrum of normal human lung cells collected from a frozen tissue sample using 50 laser pulses at approximately 20 mW.

FIG. 5B is a mass spectrum of normal human lung cells collected from a frozen tissue sample using 75 laser pulses.

FIG. 5C is a mass spectrum of normal human lung cells collected from a frozen tissue sample using 100 laser pulses at approximately 20 mW.

FIGS. 6A-1 to 6A-4 are photographs of a frozen tissue section (6A-1) and an LCM captured sample (6A-2), and mass spectra (low mass, 6A-3 and high mass, 6A-4) of normal stroma cells from a human breast tissue sample.

FIGS. 6B-1 to 6B-4 are photographs of a frozen tissue section (6B-1) and an LCM captured sample (6B-2), and mass spectra (low mass, 6B-3 and high mass, 6B-4) of normal epithelium cells from a human breast tissue sample.

FIGS. 6C-1 to 6C-4 are photographs of a frozen tissue section (6C-1) and an LCM captured sample (6C-2), and mass spectra (low mass, 6C-3 and high mass, 6C-4) of ductal carcinoma in situ from a human breast tissue sample.

FIGS. 6D-1 to 6D-4 are photographs of a frozen tissue section (6D-1) and an LCM captured sample (6D-2), and mass spectra (low mass, 6D-3 and high mass, 6D-4) of invasive ductal carcinoma from a human breast tissue sample.

FIGS. 6E-1 to 6E-4 are a photographs of a frozen tissue section (6E-1) and an LCM captured sample (6E-2), and mass spectra (low mass, 6E-3 and high mass, 6E-4) of metastatic to a lymph node from a human breast.

DETAILED DESCRIPTION

The new highly specific and sensitive technique for exploring cell physiology includes selecting specific cells or groups of cells by Laser Capture Microdissection (LCM) and characterizing the cells by Matrix-Assisted Laser Desorption/Ionization Mass Spectrometry (MALDI-MS).

LCM enables pathologists and researchers in genomics and proteomics to separate clusters of cells or even individual cells of interest from a background of millions of other cells. The collected cells can be directly visualized to verify their identity and purity. LCM is used to select small clusters of cells of interest from frozen sections of tissue by embedding them in a transfer film, e.g., a thermoplastic polymer. An example of a suitable thermoplastic polymer is ethylene vinyl acetate (EVA). The general methods of LCM are well known. See, e.g., U.S. Pat. Nos. 5,985,085; 5,859, 699; and 5,843,657; as well as Suarez-Quian et al., "Laser Capture Microdissection of Single Cells from Complex Tissues," BioTechniques, Vol. 26, pages 328–335 (1999); Simone et al., "Laser-capture microdissection: opening the microscopic frontier to molecular analysis," TIG, Vol. 14, pages 272–276 (1998); and Bonner et al., "Laser Capture Microdissection: Molecular Analysis of Tissue," Science, Vol. 278, pages 1481–1483 (1997).

MALDI-MS allows the simultaneous mass spectrometric characterization of a broad variety of biological molecules present in low abundance from minute specimens. Resolution of molecules >100 kDalton (kD) present in femtomole quantities in samples of a few microliters is routinely accomplished. MALDI-Time-of-Flight (TOF) can be used to identify proteins, elucidate post-translational modifications, and reveal intermolecular interactions.

Figure 1A:
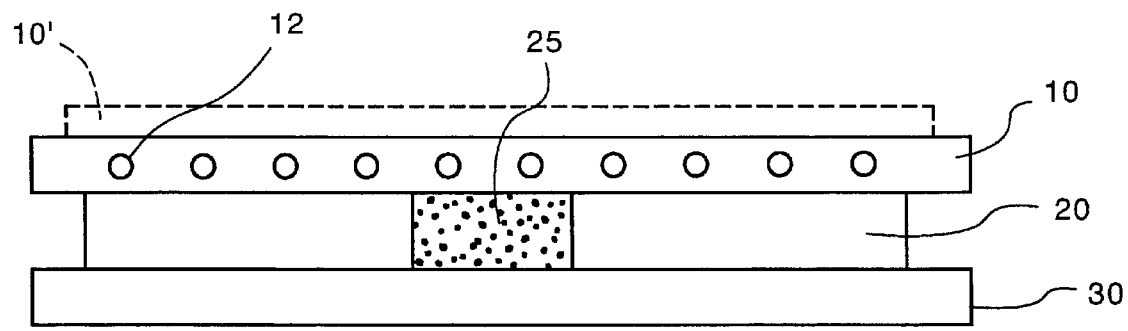
FIG. 1A is a schematic side view of a frozen tissue sample.

Referring to FIG. 1A, a transfer film 10 that inherently absorbs infrared radiation, such as EVA, that includes infrared absorbing dyes 12, is placed over a frozen tissue sample 20 which is mounted on a substrate 30, such as a glass slide. Substrate 30 is loaded into a microscope (not shown) to identify a cluster of cells 25 in frozen tissue sample 20 for mass spectroscopic analysis. Transfer film 10 can be temporarily fixed on a second substrate (film carrier) 10', which supports the film while it is being manipulated and placed onto the tissue sample. This second substrate 10' can be made of plastic, and should be a solid at room temperature, transmit both IR and visible light, and be sufficiently sturdy to support the transfer film. This substrate can be, for example, a T-100 CapSure® (Arcturus) film carrier.

Figure 1B:
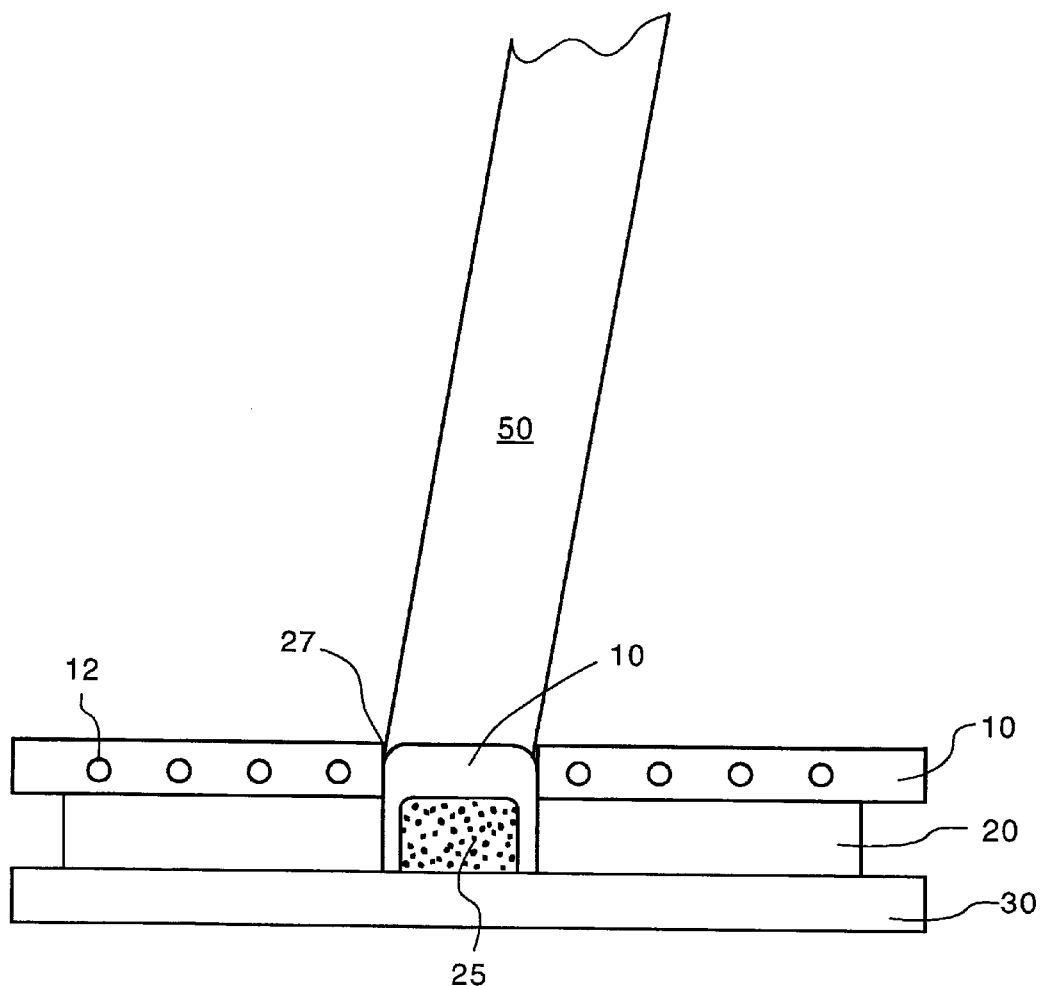
FIG. 1B is a schematic side view of the frozen tissue of FIG. 1A undergoing laser capture microdissection.

Referring to FIG. 1B, once the cluster of cells is identified, transfer film 10 is illuminated by a laser beam 50 in a region 27 around the identified cell or cells. The film or the dyes in the film absorb radiation from laser beam 50 causing transfer film 10 to melt and thereby embed cluster 25 into a portion 15 of the film. The laser beam's intensity, duration, and beam diameter control the resolution, i.e., size and amount of transfer film melted into tissue sample 20, of embedded cells. For example, a focused near-infrared laser beam can be used to melt portions of the transfer film as small as 6 microns in diameter. The diameter of a typical stromal tissue cell is about 10 microns. The laser must be able to pass through any substrate 10' to reach the transfer film 10.

Figure 2:
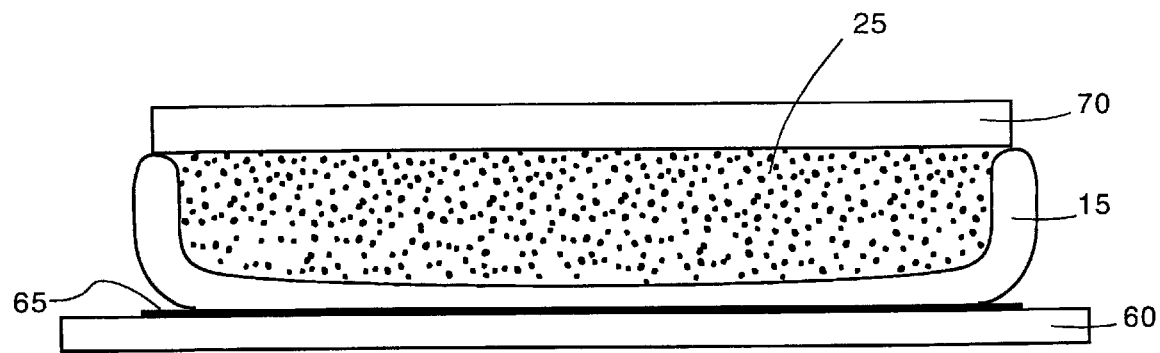
FIG. 2 is a schematic side view of a mass spectroscopic sample target including the cells embedded in the transfer film of FIG. 1B.

Referring to FIG. 2, once portion 15 and embedded cells 25 are removed from substrate 30, film portion 15 is bonded to a mass spectroscopic target plate 60 by an adhesive 65, e.g., a glue. A matrix composition 70 is applied to cells 25 which assists in the desorption and ionization of different classes of molecules when performing MALDI-MS on the embedded cells. Matrix composition 70, typically, includes an proton donor acid dissolved in an aqueous solution of 1) acetonitrile and tri-fluoroacetic acid (TFA) or 2) acetonitrile and acetic acid or 3) chloroform and methanol. Selection of solvent is due largely to the hyrophobic character of the analytes of interest, e.g., hydrophobic analytes require hydrophobic solvents. Examples of proton donor acids include but are not limited to, sinapinic acid (SA), 2,5-dihydroxybenzoic acid (DHB), alpha-cyano-4-hydroxy cinnamic acid, nicotinic acid, picolinic acid, hydroxyphenylazobenzoic acid (HABA), and ferrulic acid. The choice of matrix is governed by the gas phase ionizability of the analyte. As discussed below, certain matrices give a more dependable signal for certain types of biomolecules.

A mass spectrum of the embedded cells is recorded by creating gas-phase ions of the cellular components, separating the ions in space or time based on their mass-to-charge ratio, and measuring the quantity of the ions of each mass-to-charge ratio. Techniques for separating gas-phase ions include, but are not limited to, time-of-flight (TOF), ion-trap, magnetic-sector, quadrupole mass filter, and ion cyclotron resonance.

Figure 3:
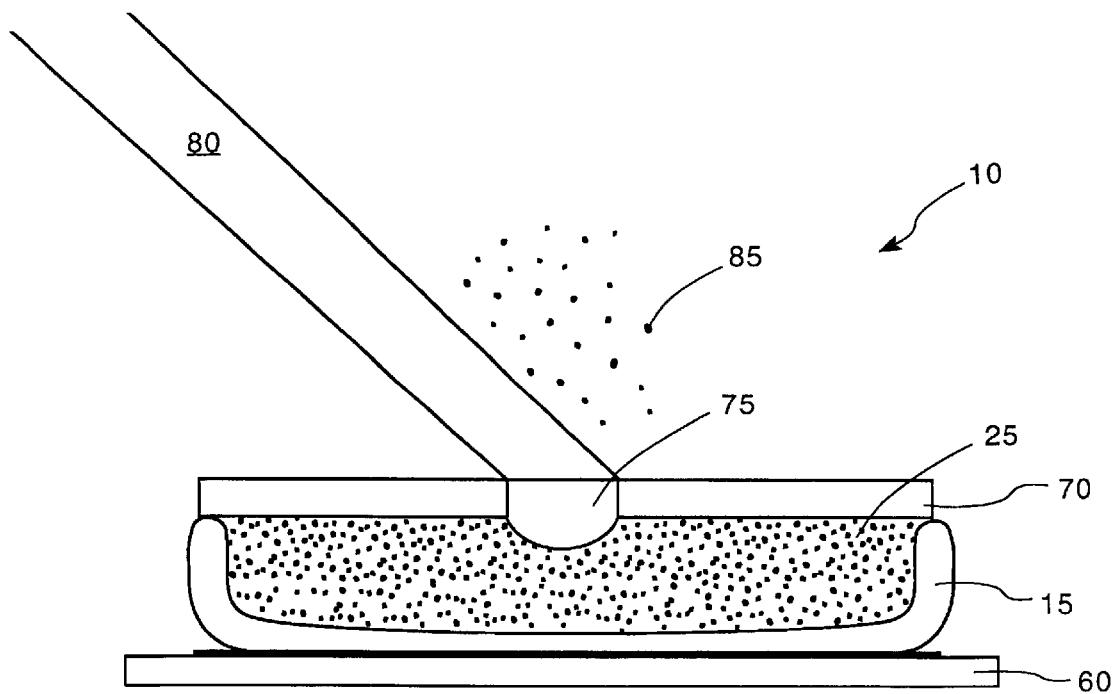
FIG. 3 is a schematic view of the mass spectroscopic sample target of FIG. 2 in a mass spectroscopy instrument.

Referring to FIG. 3, target plate 60 is loaded into a mass spectroscopic instrument 10 and a laser beam 80 ablates a portion 75 of matrix composition 70 and cells 25 to vaporize the matrix and cellular components 85, e.g., proteins, peptides, and nucleic acids. During laser ablation, the proton donor acid donates a proton to the vaporized cellular components, thereby producing gas-phase cellular component ions which are subsequently separated and measured according to their mass weight by any of the techniques discussed above.

The type of proton donor acid used in the matrix composition depends on the type of biological material being analyzed. The role of the proton donor acid is to provide one or more positive charges to the analyte. Preferably, the proton donor acid provides a single proton to the biological component of interest thereby creating a positively-charged biological compound and a negative donor acid compound. If the proton donor acid provides multiple protons, the biological component of interest can be fragmented undesirably into several smaller mass components. Typically, sinapinic acid is used in matrix compositions to create ions of proteins, 2,5-dihydroxybenzoic acid is used to create ions of nucleic acids and lipids, alpha-cyano-4-hydroxy cinnamic acid is used to create ions of peptides, and HABA is used to create ions of glycoproteins.

The choice of matrix generally affects the analytes that can be studied, but the usefulness of matrices over analyte types is not exclusive. The choice of sinapinic acid reflects an expectation that the dominant signal for diagnostic purposes will arise from proteins. In previous work with sinapinic acid on prokaryotic systems, roughly 90% of the signal comes from proteins and 10% is due to oligosaccharides. See e.g., Conway et al., J. Mol. Microbiol. Biotechnol. (in press, 2000). Additionally, one would not expect to see DNA in a heterogeneous mixture because DNA is comparatively fragile in the gas phase. Due to the high laser intensities required for ionization of heterogeneous media one would expect the DNA to be fragmented beyond recognition.

The methods and materials described herein are also discussed in Palmer-Toy et al., "Direct-Acquisition of Matrix-assisted Laser Desorption/Ionization Time-of-Flight Mass Spectra from Laser Capture Microdissected Tissues," Clinical Chemistry, Vol. 46, No. 9, pages 1513–1516 (2000).

The invention is further described in the following examples, which do not limit the scope of the invention described in the claims.

EXAMPLES

Cells of interest were selected from frozen tissue specimens using standard LCM methods using an Arcturus PXL-100 LCM device and a TF-100 Transfer Film Carrier. Tissue frozen sections 8 micron thick, collected on untreated glass slides, were stained with a modified Hematoxylin-Eosin method. The method is described by Emmert-Buck, et al., Science, 274:5289,998 B 1001, (1996). Cells were collected using 100–1000 pulses/film with a laser intensity of 10–60 mW over 50 msec, and a spot size ranging from 15–30 microns at 10.6 micron infrared wavelength. The process of LCM is already well understood, and conditions for best selectivity and most efficient transfer to films were employed. LCM procedures and instrumentation is available from Arcturus Engineering, Inc. located in Mountain View, Calif.

The follow discussion is based on LCM protocols provided by Arcturus. Frozen embedding is a standard way to preserve specimens and stabilize them for long-term storage and sectioning. The following steps were used.

Embedding

1. Prior to initiating the embedding procedure, an empty labeled cryomold was cooled on dry ice for 1 minute. The cryomold remained on dry ice during the entire embedding procedure.

2. Once cooled, the bottom of the cryomold was covered with a standard embedding medium, e.g., an inert viscous compound such as TISSUE-Tek O.C.T.®, a product of (Sakura Finetek USA).

3. The frozen tissue was placed against the bottom. To facilitate cutting, the tissue should be relatively small (1 cm) and the desired cutting surface should be flush against the bottom.

4. The cryomold was filled with embedding medium, the dry ice container was covered, and the embedding medium was allowed to harden into a block (it will turn white when frozen).

5. The block was wrapped in foil and kept at −80° C. until cutting.

Cutting

1. The block was removed from the cryomold (if not already done) and attached to a chuck in the cryostat with embedding medium. The cutting surface should be as parallel as possible.

2. The block was allowed to equilibrate to the cryostat temperature (−20° C.) for about 15 minutes.

3. 10 micron (or thinner) sections were cut onto plain uncoated glass slides.

4. The slides were kept in the cryostat or on dry ice if LCM is to be performed that day.

Transfer

For optimal transfer of frozen tissue sections, the section should be kept <10 micron thick. Thicker sections are more difficult to visualize. If there are folds in the tissue, the transfer film may not make direct contact with the entire surface at that area. Therefore, it is advisable to inspect the tissue before placing down the transfer film. If any tissue seems to be mounded or folded, it is best not to place the transfer film over that area.

The tissue section also must be dry and not cover-slipped for effective LCM transfer. The staining appears darker and more granular due to light scattered from the irregular air-tissue interface. The tissue where the polymer melts and bonds after laser activation appears lighter and resembles a cover-slipped slide due to the replacement of the air in the tissue with the polymer. This phenomenon is called index-matching or polymer wetting.

Poor transfers may result if the slide is not fully dehydrated (e.g., the 100% ethanol can become hydrated after repeated use). A final xylene rinse facilitates the efficiency of transfer with LCM. If a tissue section does not transfer well, a longer xylene rinse can be used. While other staining protocols can be used, the slides should be dehydrated in a final xylene step.

Proteolytic degradation can have deleterious effects on subsequent analysis of LCM-collected samples. To minimize proteolysis, several procedures can be used:

1. Adding protease inhibitors, such as 0.5 mM PMSF and 5 mM epsilon-aminocaproic acid to the tissue staining baths, helps suspend the proteolytic degradation of the biomarkers caused by endogenous proteolytic enzymes.
2. Keeping the duration of the LCM and capture time to less than 20 minutes after staining also reduces proteolysis. Samples are stored on dry ice or at or below 20° C. at all other times.
3. The use of other tissue staining protocols, such as toludine blue or hematoxylin without eosin makes visualization during the laser capture procedure more difficult, but the absence of the acid eosin may improve the MALDI signal, as eosin has been known to compromise other analytical protein methods.

The transfer film was gently peeled from the tissue sample and attached to a standard mass spectrometer stainless steel target using common rubber cement. The rubber cement does not produce detectable peaks above 200 Dalton (D) in the mass spectra.

Approximately 1 $\mu l/mm^2$ of a MALDI-MS matrix solution was uniformly distributed using a hand held pipetter over captured cells embedded in the transfer film. Various matrices were employed to favor the desorption and ionization of different classes of molecules. Results were obtained using saturated sinapinic acid, 10 mg/ml of 2,5-dihydroxybenzoic acid, and alpha-cyano-4-hydroxy cinnamic acid in 20–70% acetonitrile and 0.1% trifluoroacetic acid.

MALDI-TOF spectra are collected in positive-ion mode using Bruker Reflex II, Reflex III and Biflex III MALDI-TOF mass spectrometers operated in linear mode. Acceleration voltages are between about 16 and about 25 kV, with an optimal range between about 18 and about 20 kV. Pulsed ion extraction voltages of about 14 to about 19 kV were employed. Detector voltages of about 1.4 to about 1.7 kV are possible, with optimal response at about 1.6 kV. The MALDI laser was a 75 mW, 337 nm, 4 ns pulse, UV laser. Digitizer settings were set to record the mass/charge range of 2–70 kD. Ion suppression below m/z =3 kD was used to prevent detector saturation in the low mass range.

Acquisition consisted of 500 MALDI shots, which were summed into a buffer in 10 groups of 50 shots. Each 50-shot acquisition group occurred on small clusters of MALDI crystals that yielded signal containing resolved peaks in the 2–70 kDa domain of interest. Acquisition of the 10 information-containing groups of shots was possible by surveying roughly 25 small groups of crystals, with a 40% success rate and a 60% failure rate. Any failure to observe spectra was due to poor ionization, which was usually due to either poor crystallization of the MALDI matrix or the absence of analyte molecules in the crystal. It can be possible that successful acquisition of a protein from one small cluster of crystals is equivalent to acquisition from a single cell. The LCM/MALDI-MS protocol requires the use of many cells in the LCM step to ensure that a statistically-significant number of clearly-formed crystals have occurred in the presence of analyte molecules from captured cells. Data was processed with five-point Savitzky-Golay smoothing and baseline subtraction. See e.g., Press et al., Numerical Recipes in C, The Art of Scientific Computing, $2^{nd}$ Ed., p. 650 (Cambridge Univ. Press, Cambridge, England, 1996). Baseline subtraction was provided by a spline fit to a defined set of points chosen by the user to represent the baseline. Peaks were chosen using two methods: 1) by hand, with instrument operator judgment for peak shape, resolution, and signal-to-noise features, and 2) using a peak finding algorithm that mimics the complex decision making features of the common MALDI-TOF instrument operator. Spectral similarities and differences were obtained using two techniques: 1) by eye, and 2) using an algorithm that quantifies the differences between spectral peak lists.

EXAMPLE 1

Mass Spectra of Normal Human Lung Epithelial Cells and Malignant Human Lung Epithelial Cells from a Pulmonary Adenocarcinoma LCM cells were collected using 400 pulses/film with a laser intensity of 10–60 mW over 50 msec, and a spot size ranging from 15–20 microns. Saturated sinapinic acid in 50% acetonitrile and 0.1% trifluoroacetic acid were used as the MALDI-TOF matrix. Referring to FIGS. 4A and 4B, the mass spectrum of normal lung cells is distinct from the mass spectrum of malignant human lung cells. For example, each mass spectrum contains about 20–40 well-resolved peaks spanning from 3 to 20 kDalton (kD) and the normal lung cell mass spectrum contains two strong features between about 15 to about 16 kD which are either absent or very weak in the mass spectrum of malignant lung cells. Additionally, the mass spectrum of malignant lung cells contains two strong features between about 3 to about 4 kD which are either absent or very weak in the mass spectrum of normal lung cells.

Spectral reproducibility has been demonstrated from point to point on the same target and from tissue sample to tissue sample in the same patient. Point-to-point reproducibility is obtained by comparing the 10 groups of 50 MALDI laser pulses. MALDI spectra are sufficiently reproducible for the construction of a database of spectra representing tissue types and tissue disease states.

EXAMPLE 2

Number of Cells Collected as a Function of Number of Laser Pulses

Sensitivity of the method was explored by capturing specific cells with 25, 50, 75, and 100 laser pulses, respectively, in four quadrants of a transfer film. The film was subsequently quartered, and each piece was separately examined as described above.

The tissue was normal human lymph node. The laser intensity was 10–60 mW over 50 msec, with a spot size ranging from 15–20 microns. These settings corresponded to approximately 5 cells per pulse, on average. Saturated sinapinic acid in 50% acetonitrile and 0.1% trifluoroacetic acid were used as the MALDI-MS matrix.

As shown in FIGS. 5A, 5B, and 5C, the quality of the signal, as measured in terms of well-resolved mass spectral peaks between about 15 and about 20 kD, improved steadily with increasing pulse density up to 75 pulses/quarter film. The increasing density of LCM captured cells increases the likelihood of proper crystallization of the matrix on a captured cell.

EXAMPLE 3

The Effects of Varying MALDI-MS Matrix Compositions

The influence of acetonitrile on the extraction efficiency of proteins from the transfer film was tested by recording several mass spectra of LCM tissue samples of microdissected lymph nodes with matrix compositions containing different concentrations of acetonitrile. For example, saturated sinapinic acid with 0.1% trifluoroacetic acid was used with 20, 25, 30, 35, 40, 50, 60, and 70% acetonitrile. Acetonitrile concentrations ranging from about 25 to about 50% were found to work adequately, but the most information dense spectra with this type of LCM tissue were obtained by using about 30% acetonitrile.

10 mg/ml of 2,5-dihydroxybenzoic acid in about 30% acetonitrile and 0.1% trifluoroacetic acid also yielded the mass spectra similar to the mass spectra recorded with sinapinic acid and about 30% acetonitrile.

EXAMPLE 4

Specificity of the LCM/MALDI-MS Method

The ability of the LCM/MALDI-MS method to select and analyze specific cell populations was tested by separately microdissecting (by LCM) four cell types from a single frozen section of human breast ductal carcinoma, i.e., normal breast epithelium, normal breast stroma, ductal carcinoma in situ, and invasive ductal carcinoma.

Each sample was collected with 1000 pulses/film from a laser having an intensity of 10–60 mW over 50 msec and a spot size ranging from 15–20 microns. Saturated sinapinic acid in 30% acetonitrile and 0.1% trifluoroacetic acid was used as the MALDI-MS matrix composition.

As shown in FIGS. 6A1-4, 6B1-4, 6C1-4, and 6D1-4, four distinct mass spectra were obtained from the four cell types. In addition, a frozen section of ductal carcinoma metastatic to a lymph node was also available from the same patient and was compared to the LCM dissected tissues. See also FIG. 6E1-4. The metastatic tumor spectrum resembled the spectra from the primary tumor in FIGS. 6D3 and 6D4. The carcinoma in situ spectrum has features intermediate between the normal epithelium and the invasive tumor.

Figures 1, 2, 6A:
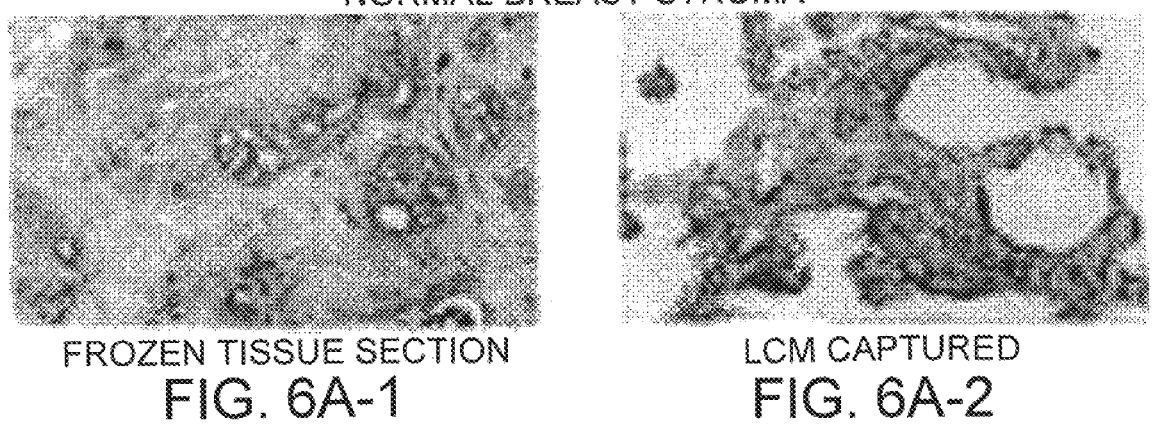
Figures 1, 6B:
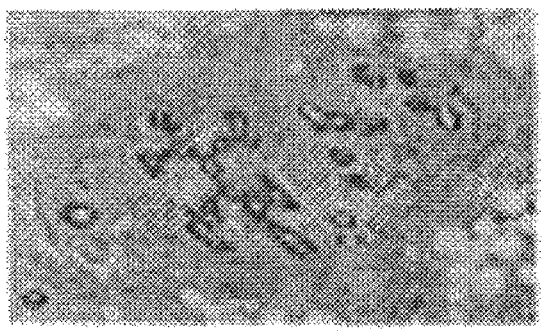
Figures 2, 6B:
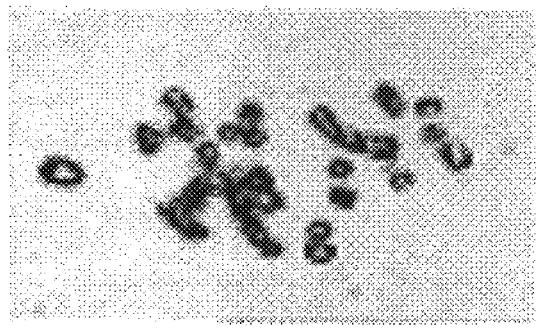
Figures 4, 6B:
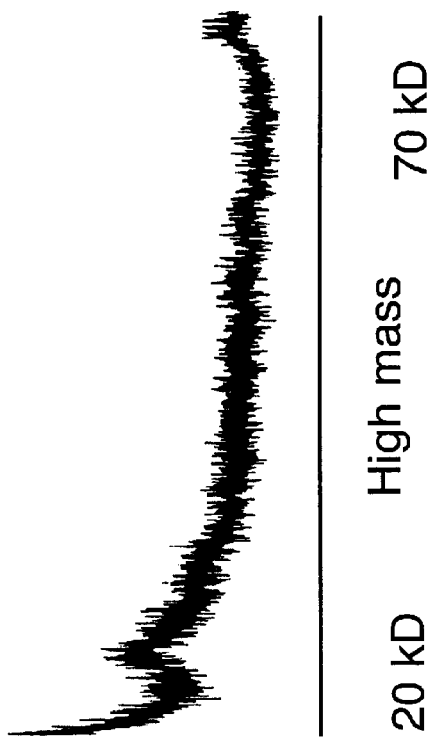
Figures 3, 6B:
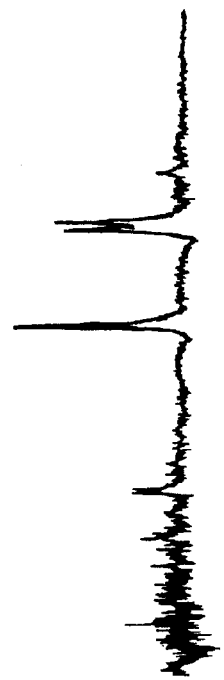

A comparison of the low mass spectra in FIGS. 6A-3 and 6B-3 gave largely similar profiles. The peaks at about 11440, about 13950, and about 14167 have no discriminating value. The normal stroma has peaks at about 11724 and about 12363 that differentiate it from the normal epithelium. In the range below 10 kD, several peaks indicate stroma rather than epithelium. High mass spectra reveal discriminating features below the putative 68 kD albumin peak.

Figures 1, 2, 6C:
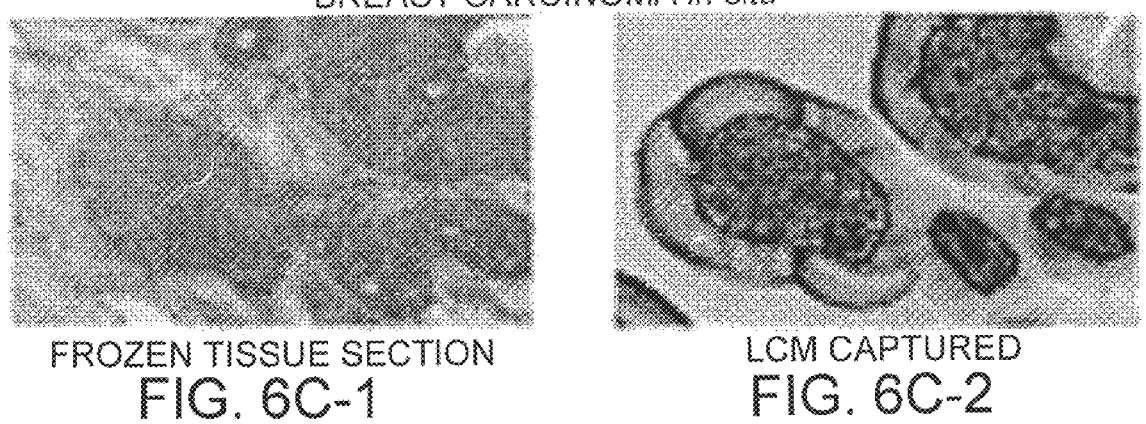
Figures 4, 6C:
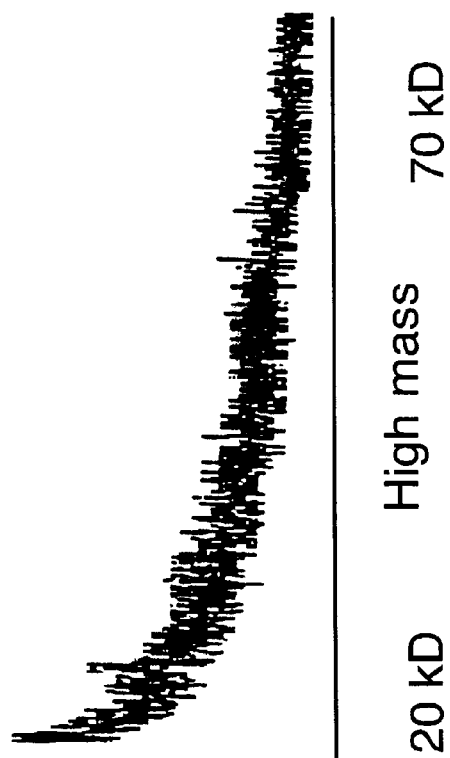
Figures 3, 6C:
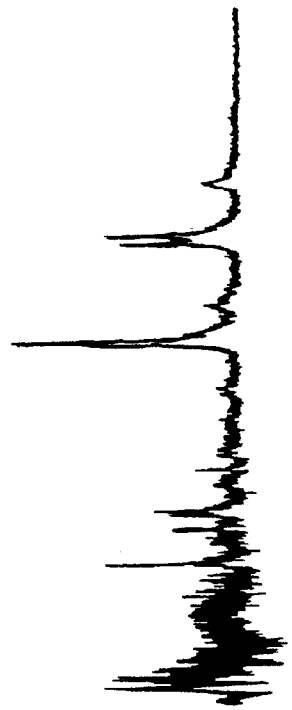

A comparison of the low mass spectra in FIGS. 6B-3 and 6C-3 shows similarities and differences between normal and cancerous epithelial tissues. Peaks at about 9487, about 12366, and about 15502 are indicative of carcinoma in situ. A visual inspection of the figures reveals other peaks that differentiate the two tissue types. Typically, the high mass spectra are nonindicative. However, epithelial carcinoma in situ is demonstrably different from normal stroma at high mass, just as healthy epithelial tissue is also different from normal stroma.

Figures 1, 6D:
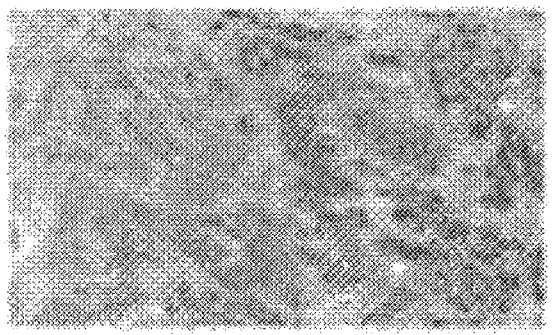
Figures 2, 6D:
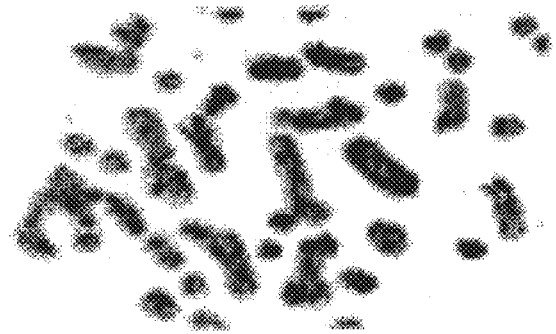
Figures 4, 6D:
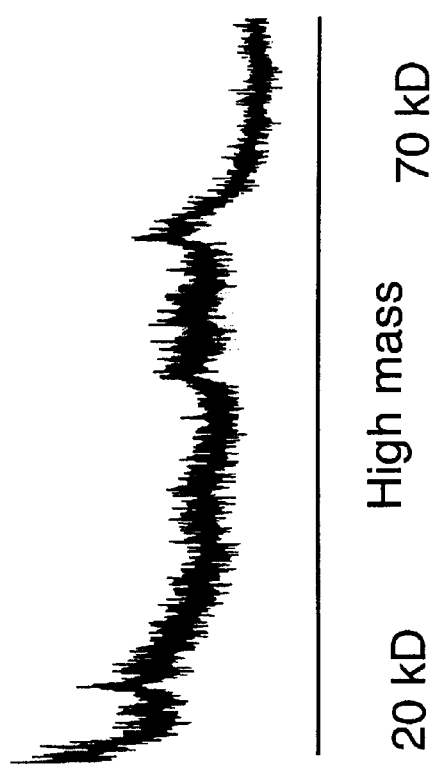
Figures 3, 6D:
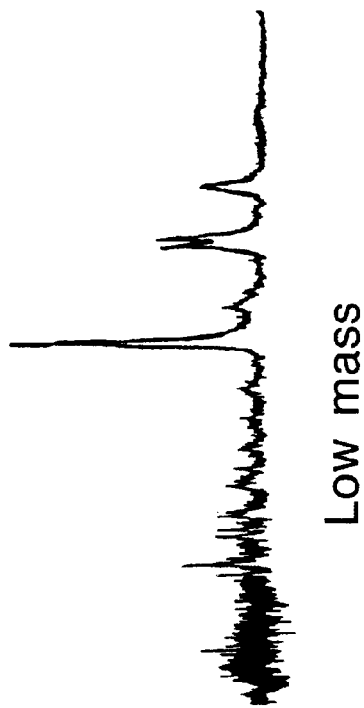

A comparison of the low mass spectra in FIGS. 6C-3 and 6D-3 shows similarities and differences between carcinoma in situ and invasive carcinoma. The principal peaks at about 9487 and above are all nearly identical, suggesting that each is a marker in cancerous tissue. Subtraction of the normal epithelium peaks from these spectra would help to indicate which features of these spectra are uniquely indicative of cancer. The peak at about 8681 and broader peaks at high mass help to distinguish the invasive cancer from the carcinoma in situ.

Figures 1, 6E:
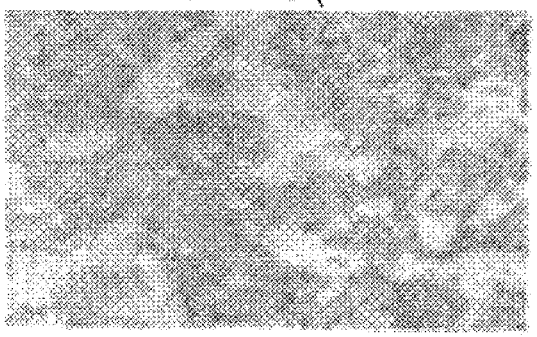
Figures 2, 6E:
Figures 4, 6E:
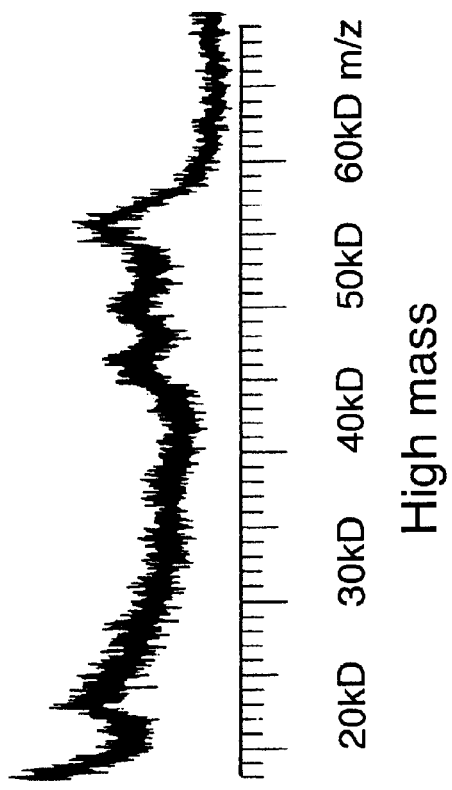
Figures 3, 6E:
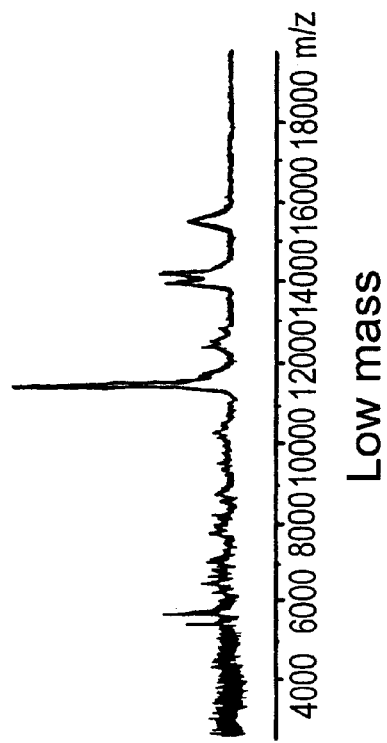

A comparison of the low mass spectra in FIGS. 6D-3 and 6E-3 shows similarities between invasive carcinoma of the breast and metastatic carcinoma of the lymph node. The peak at about 8681 and the broader peaks at high mass remain definitive markers for aggressive cancer states, either metastatic or invasive. Peaks at about 10255 and about 10107 distinguish between the invasive and metastatic cancers.

The above analysis indicates some, but not all, of the biomarkers in the MALDI profiles of LCM tissue that are seen to distinguish between tissue types.

EXAMPLE 5

Use of Methods to Avoid Proteolytic Degradation

Figure 7A:
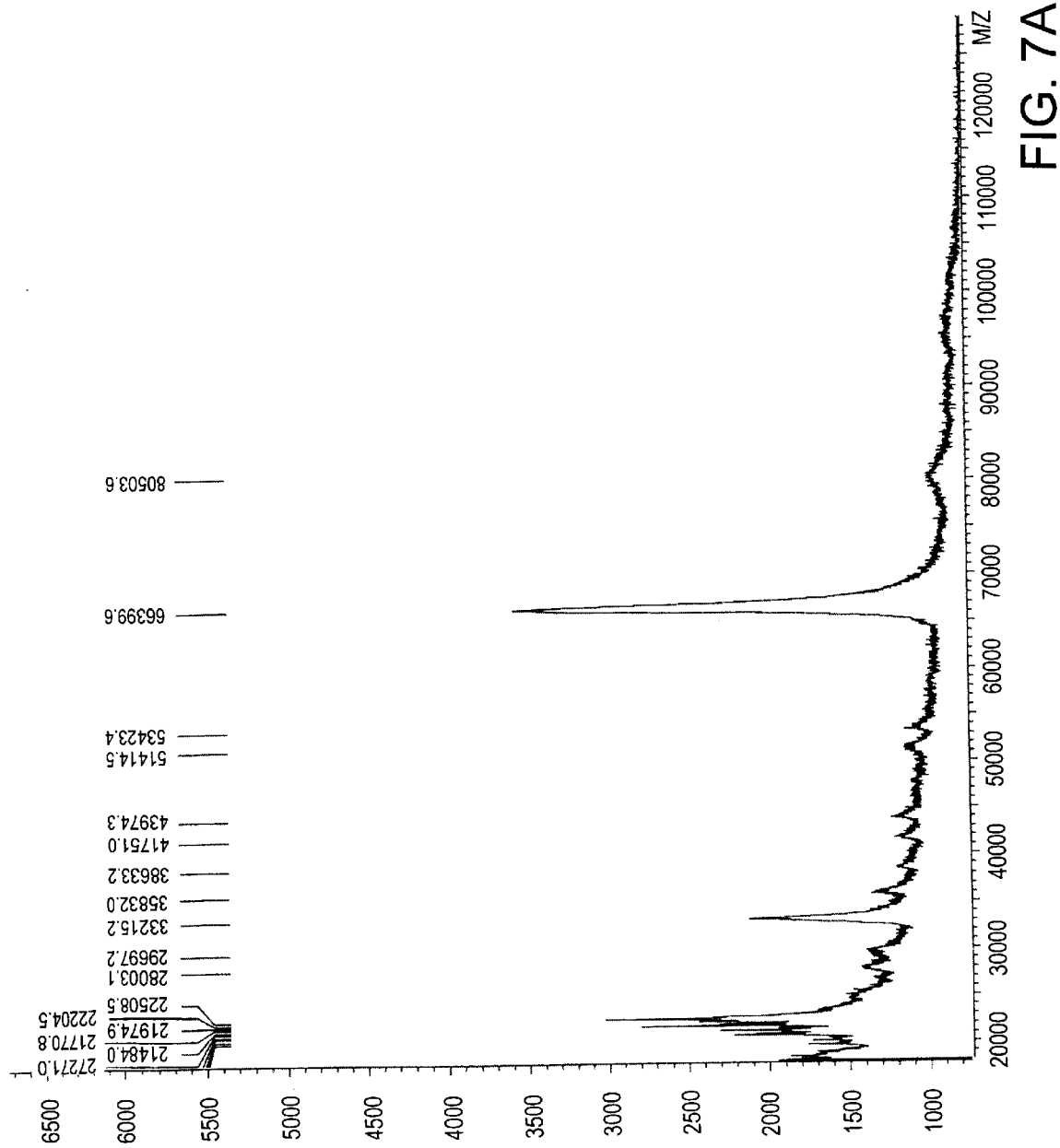
FIG. 7A is a mass spectrum of healthy human epithelium obtained using sample preparation and handling methods that avoid proteolytic degradation, i.e., using protease inhibitors, avoiding the use of eosin, and using rapid (<20 minute) collection times. Data is presented without baseline subtraction.
Figure 7B:
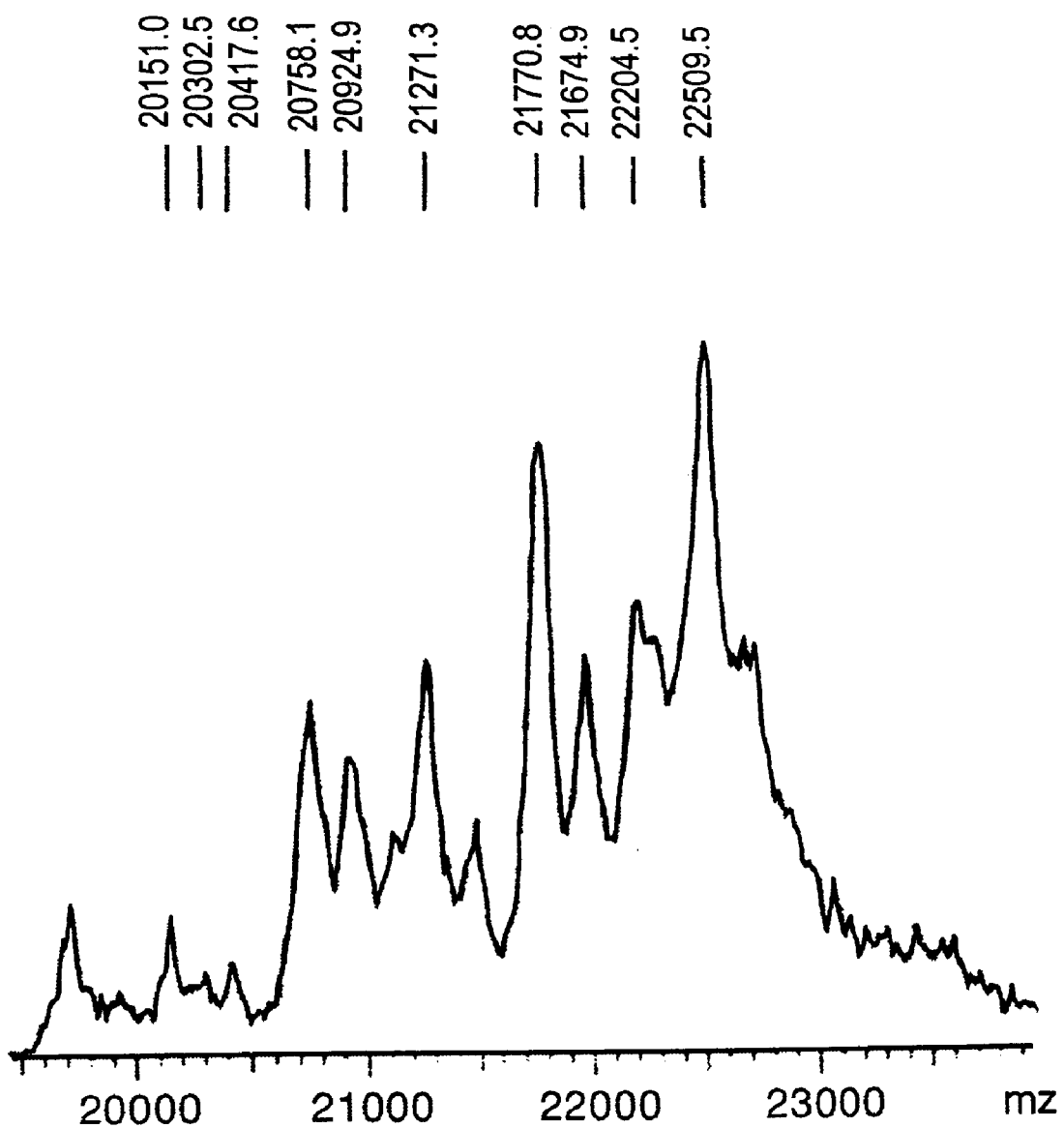
FIG. 7B is a low mass (19.5 kDa to 23.5 kDa) enlargement of the spectrum of FIG. 7A.

The use of the improved tissue handling procedures described herein that avoid proteolytic degradation greatly improve the overall resolution and sensitivity of the LCM-MALDI process, especially in mass domain above 18 kDa. The masses in FIG. 7A in the range from 20–50 kD also show lower relative intensities, but much higher resolutions than the equivalent masses in FIG. 6A. In FIG. 7B, a complex signal between 19–23 kD contrasts with the total absence of signal in FIG. 6A in the same range. Lastly, since both spectra represent normal epithelium tissue, it is gratifying to note that the general spectral features are the same. The tissue in FIG. 7A was taken from a patient other than the tissue donor in FIG. 6A, and the analysis was performed on a different instrument almost a year later. While signal enhancement is clearly present, the basic feature of reproducibility is not lost.

OTHER EMBODIMENTS

In other embodiments, mass spectra recorded from a LCM tissue sample can be compared against a standard library of mass spectra of tissue samples to determine if the LCM tissue sample is normal or abnormal, e.g., containing a carcinoma.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a mass spectrum of a tissue sample, the method comprising:

covering a tissue sample with a polymer, identifying one or more specific cells of the tissue sample for mass spectrometric analysis, melting a portion of the polymer to cause the portion of the polymer to adhere onto the specified cells of the tissue sample and allowing the polymer to solidify, removing at least the portion of the polymer containing the specified cells from the tissue sample, attaching the portion of the polymer to a mass spectrometric target, applying a matrix composition to the specified cells, and determining the mass spectrum of the specified cells by matrix assisted laser desorption ionization mass spectrometry.

2. The method of claim 1, wherein the matrix composition includes a proton donor acid.

3. The method of claim 2, wherein the proton donor acid is selected from the group consisting of sinapinic acid, 2,5-dihydroxybenzoic acid, alpha-cyano-4-hydroxy cinnamic acid, nicotinic acid, and ferrulic acid.

4. The method of claim 3, wherein the proton donor acid is sinapinic acid.

5. The method of claim 1, wherein the matrix composition includes acetonitrile.

6. The method of claim 1, wherein determining the mass spectrum further includes ionizing the specified cells on the polymer.

7. The method of claim 1, wherein determining the mass spectrum includes separating gas-phase ions by time-of-flight (TOF) measurements, ion-trap measurements, magnetic-sector measurements, quadrupole mass filter measurements, or ion cyclotron resonance measurements.

8. The method of claim 7, wherein the gas-phase ions are separated by time-of-flight measurements.

9. The method of claim 1, wherein the entire polymer is removed from the tissue sample.

10. The method of claim 1, wherein the polymer is attached to a substrate.

11. The method of claim 10, wherein the polymer is removed from the substrate and thereafter attached to the mass spectrometric target.

12. A method of determining a mass spectrometric profile of a tissue sample, the method comprising:

selecting specific cells of the tissue sample by laser capture microdissection, and determining a mass spectrum of the selected cells by matrix assisted laser desorption ionization mass spectrometry.

13. The method of claim 12, wherein determining the mass spectrum of the selected cells includes applying a matrix composition to the selected cells.

14. The method of claim 13, wherein the matrix composition includes a proton donor acid.

15. The method of claim 14, wherein the proton donor acid is selected from the group consisting of sinapinic acid, 2,5-dihydroxybenzoic acid, alpha-cyano-4-hydroxy cinnamic acid, nicotinic acid, and ferrulic acid.

16. The method of claim 15, wherein the proton donor acid is sinapinic acid.

17. The method of claim 13, wherein the matrix composition includes acetonitrile.

18. The method of claim 12, wherein determining the mass spectrum further includes ionizing the selected cells on a thermoplastic polymer.

19. The method of claim 12, wherein determining the mass spectrum includes separating gas-phase ions by time-of-flight (TOF) measurements, ion-trap measurements, magnetic-sector measurements, quadrupole mass filter measurements, or ion cyclotron resonance measurements.

20. The method of claim 19, wherein the gas-phase ions are separated by time-of-flight measurements.

21. A method of characterizing tissue samples, the method comprising:

selecting specific cells of a tissue sample by laser capture microdissection, determining a mass spectrum of the selected cells by matrix assisted laser desorption ionization mass spectrometry, and comparing the mass spectrum of the selected cells against a standard library of mass spectra of tissue samples.

22. The method of claim 21, wherein the tissue samples in the standard library are selected from the group consisting of normal breast stroma, normal breast epithelial, breast carcinoma in situ, invasive breast carcinoma, and metastatic lymph node carcinoma.

23. A method of determining whether a tissue sample includes cancer cells, the method comprising characterizing the tissue sample by the method of claim 21, wherein the library of mass spectra includes spectra of both normal and cancerous tissues.

* * * * *